United States Patent [19]

Giurtino

[11] Patent Number: 4,595,641
[45] Date of Patent: Jun. 17, 1986

[54] BATTERY COMPARTMENT HAVING BATTERY POLARITY PROTECTION

[75] Inventor: Joel F. Giurtino, Miami, Fla.

[73] Assignee: Cordis Corporation, Miami, Fla.

[21] Appl. No.: 736,570

[22] Filed: May 21, 1985

[51] Int. Cl.⁴ .............................................. H01M 2/10
[52] U.S. Cl. .......................................... 429/1; 429/99
[58] Field of Search ................. 429/1, 97, 98, 99, 100, 429/156, 157

[56] References Cited

U.S. PATENT DOCUMENTS

| | | | |
|---|---|---|---|
| 2,293,354 | 8/1942 | Munchow | 429/1 |
| 3,990,919 | 11/1976 | Krueger | 420/100 |

Primary Examiner—Donald L. Walton
Attorney, Agent, or Firm—Lockwood, Alex, FitzGibbon & Cummings

[57] ABSTRACT

A battery compartment providing reverse-polarity and reduced voltage protection for a portable battery-powered electronic apparatus includes an elongated chamber for receiving a plurality of series-connected standard "D"-type battery cells. Positive and negative polarity electrical contact assemblies at each end of the chamber engage the positive and negative end terminals of the serially connected battery cells when the cells are properly orientated in the compartment. When the batteries are misoriented, an insulating member on the positive contact assembly prevents electrical contact with the negative battery terminal, and an insulator member on the negative contact assembly prevents electrical contact with the positive battery cell terminal.

17 Claims, 11 Drawing Figures

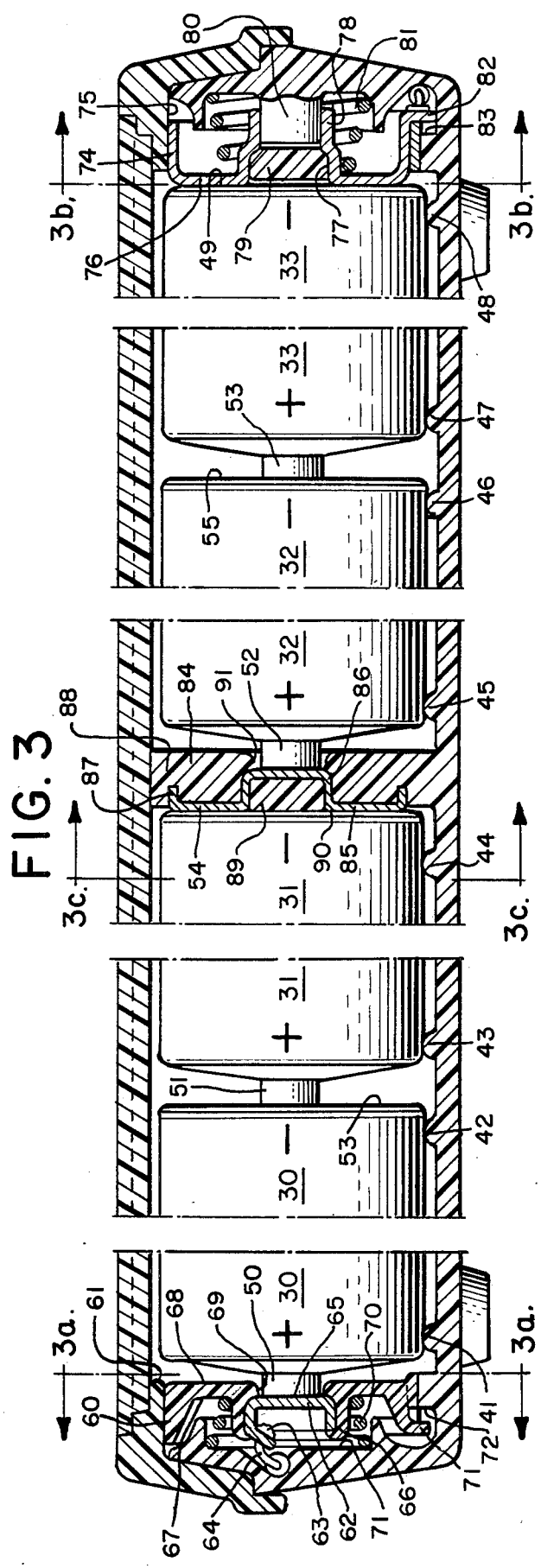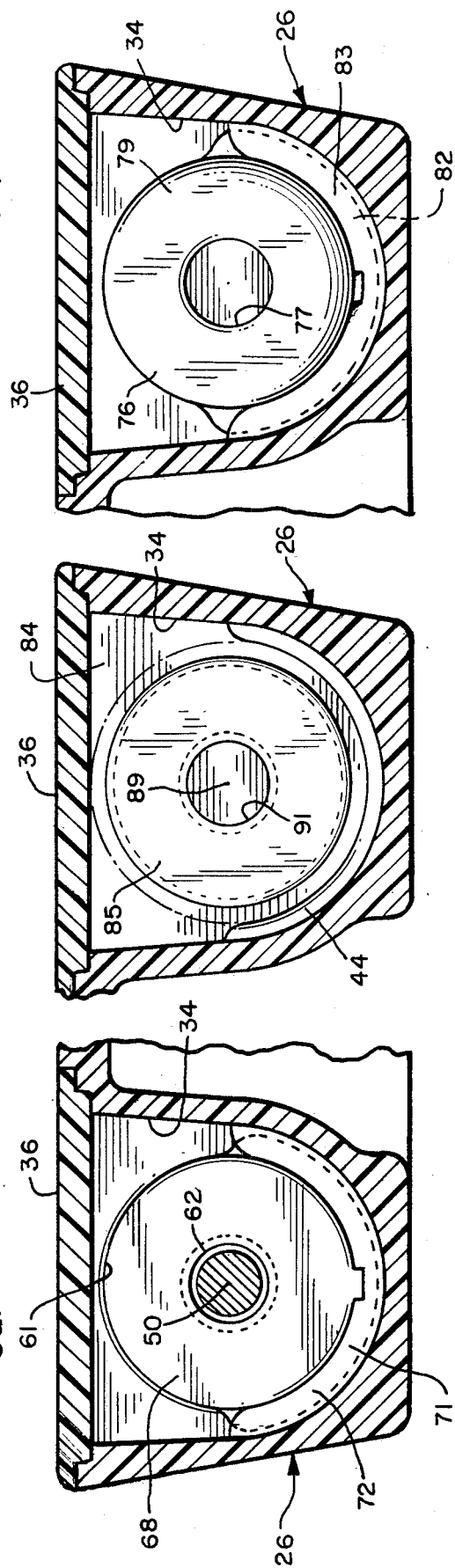

BATTERY COMPARTMENT HAVING BATTERY POLARITY PROTECTION

BACKGROUND OF THE INVENTION

The present invention relates generally to portable battery operated electronic equipment, and more particularly to a battery compartment for use with such equipment in which electrical connection to the battery is prevented in the event one or more of the cells thereof is incorrectly oriented within the compartment. The compartment is particularly well suited for use in battery operated medical electronic equipment such as, for example, a cardiac pacer system analyzer.

Safety in the use of electrically operated equipment during treatment of a medical disorder requires that adequate measures be taken to prevent inadvertent patient exposure to potentially endangering electrical currents. While efforts directed to preventing such contact have proven effective, patient safety can be further enhanced by removing all high voltage sources from the vicinity of the patient. The use of low voltage electrochemical cells to power medical electronic equipment is therefore attractive since step-down power supplies, and the relatively high voltage alternating current required for their operation, can be entirely eliminated.

While battery operation is attractive from the viewpoints of safety and portability, these benefits are not derived without some cost. In particular, the need for periodic user-replacement of the battery enhances the probability that one or more of the battery cells will be incorrectly polarized within the battery compartment, resulting in incorrect battery voltage or polarity, a general deterioration of equipment performance, and possible damage to equipment circuitry. It is therefore desirable to reduce or eliminate the possibility of such inadvertent misorientation of cells within a battery compartment. Accordingly, electronic as well as mechanical techniques have been employed to avoid the adverse consequences of incorrect cell orientation.

One well known electronic technique is the provision of semiconductor diodes in the battery circuit to prevent the application of reverse voltages to polarity sensitive circuit components. While this technique is effective in preventing circuit damage in the event of incorrect battery polarity, it is ineffective when only one or two cells of a multi-cell battery are misoriented since, in such a case, the resulting battery voltage will not be of opposite polarity, but will merely be of lower amplitude. Furthermore, the voltage drop across one or more forward biased diodes during normal operation may significantly reduce available battery voltage.

Mechanical techniques have generally been utilized in conjunction with battery types in which the battery terminals are either asymmetrically located on the battery casing or are of differing size or shape. Preferably the differences between the positive and negative polarity battery terminals are such that respective battery compartment contacts can only engage one or the other of such terminals. This technique has typically been employed in conjunction with relatively more expensive single-unit, multi-cell, batteries rather than with the more inexpensive cylindrical "D" or "C" electrochemical cells having terminals on opposite ends.

The present invention is directed to a battery compartment for receiving one or more cylindrical electrochemical cells of the type having terminals at opposite ends. The battery compartment includes terminals constructed so as to establish electrical contact with one or the other, but not both, of the terminal types utilized in such cells. In a battery compartment constructed in accordance with the invention, electrical continuity between the battery and the device circuitry will be established only if each of the cells is correctly oriented within the battery compartment.

In view of the foregoing it is a general object of the present invention to provide a new and improved battery compartment for battery operated electronic apparatus.

It is a more specific object of the present invention to provide a battery compartment which guards against inadvertent misorientation of battery cells within.

It is a still more specific object of the present invention to provide an improved battery compartment in which the battery is automatically disconnected from the apparatus circuitry in the event one or more cells are misoriented within the compartment.

SUMMARY OF THE INVENTION

A battery compartment for use with a portable battery operated electronic apparatus is provided for receiving one or more elongated electrochemical cells of the type having a protruding terminal of one polarity at one end and a generally flat terminal of opposite polarity at the other end. The battery compartment includes a first contact having a raised insulating region over its surface except over an area in contact with the protruding terminal of the cell. A second contact is provided and is arranged to engage the generally flat terminal of the cell. The second contact is provided, adjacent its center, with an insulating region having a dimension greater than that of the protruding terminal of the cell but less than that of the flat terminal. The raised insulating region of the first contact prevents electrical contact between the flat terminal of the cell and the first contact, while the second insulating region prevents contact between the protruding terminal of the cell and the second contact. Accordingly, electrical connection to the contacts and the cell terminals will be made only if the cell is properly oriented within the battery compartment.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 3 is a cross-sectional view of the battery compartment illustrated in FIG. 1 taken along line 3—3 thereof.

FIGS. 3a, 3b and 3c are cross-sectional views of the battery compartment illustrated in FIG. 3 taken along lines 3a—3a, 3b—3b and 3c—3c thereof, respectively.

DESCRIPTION OF THE PREFERRED EMBODIMENT

Figure 1:
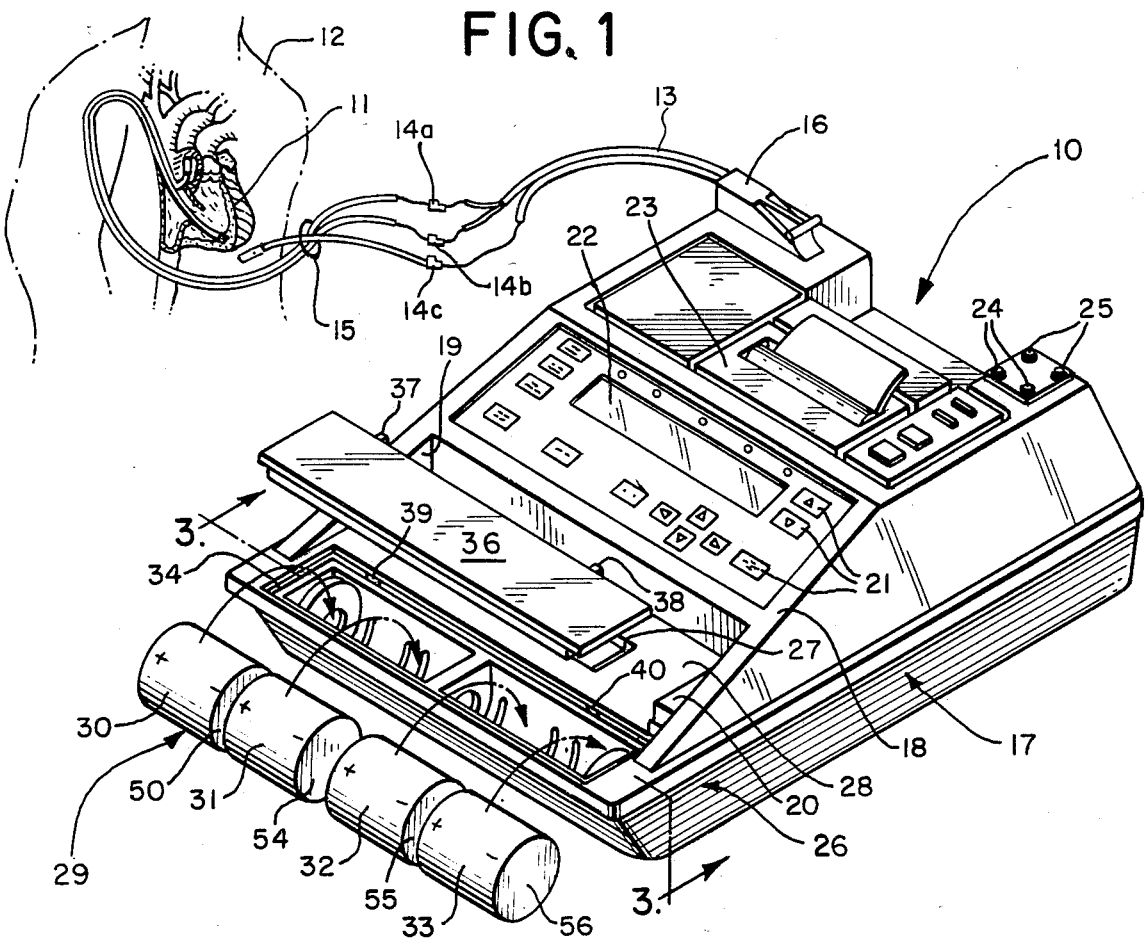
FIG. 1 is a perspective view of a portable battery-operated pace system analyzer having a battery compartment constructed in accordance with the present invention.

Referring to the figures, and particularly to FIG. 1, a pacer system analyzer (PSA) 10 is shown which includes a battery compartment constructed in accordance with the invention. As illustrated, the PSA is connected to the heart 11 of a patient 12 by means of a patient cable assembly 13 which connects through a plurality of clip leads 14a, 14b and 14c to one end of a conventional pacer lead 15. The other end of the pacer lead is implanted within the heart in accordance with conventional practice. The remaining end of the patient cable assembly 13 is connected to PSA 10 by means of a multi-contact connector 16.

PSA 10 is contained within a generally rectangular housing 17 formed of a durable, insulating, plastic or like material and includes a sloping, generally flat, control panel 18. A portion of the housing is formed to provide a receptacle 19 for receiving a sealed package (not shown) containing a sterile implantable cardiac pacer. A connector 20 in receptacle 19 engages a plurality of electrical contacts on the package to provide electrical communication between PSA 10 and the enclosed pacer.

Panel 18 includes a plurality of pressure sensitive user-actuable pushbutton controls 21 and a liquid crystal display (LCD) 22. PSA 10 operates in one of several user-selected modes in accordance with entered keystroke commands. To assist the user in selecting the appropriate operating mode, a series of internally generated instructions and a plurality of measured pacer system operating parameters are displayed on LCD 22. A printer mechanism 23 provides a printed record of measured pacer system operating parameters and measured patient parameters, while two pairs of IECG electrodes, 24 and 25, provide electrically isolated atrial and ventricular cardiac signals for connection to external instrumentation.

PSA 10 is preferably adapted for portable operation. To this end, a handle 26 is formed at one end of housing 17 by providing an elongated, generally rectangular aperture 27 through the lower surface 28 of the receptacle 19. Aperture 27 is dimensioned to permit the passage of a user's hand therethrough whereby the handle can be grasped for carrying.

To further enhance the portability of PSA 10, electrical energy for operating the unit is provided by means of a battery 29 comprising four series-connected "D" type cylindrical electrochemical battery cells 30-33. Each of these cells is contained in handle 26 within a battery compartment 34 constructed in accordance with the invention.

Figure 2:
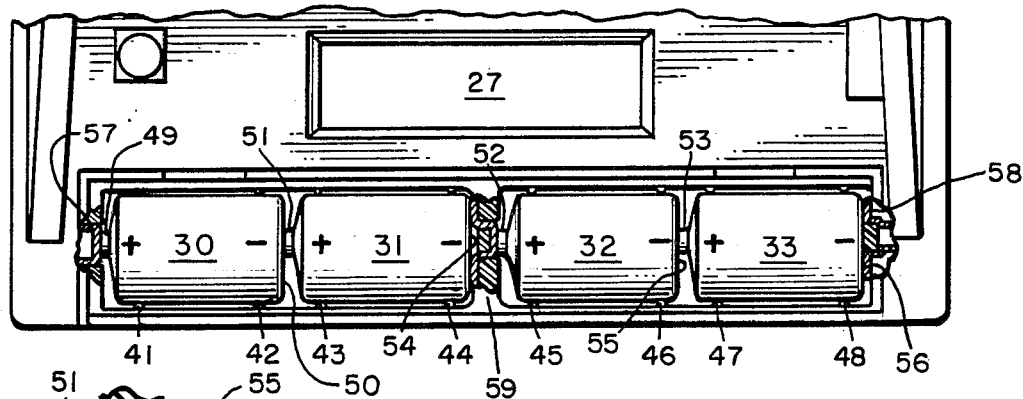
FIG. 2 is a fragmentary top plan view, partially in section, of the battery compartment illustrated in FIG. 1 showing four electrochemical battery cells positioned therein.

Referring generally to FIGS. 1-3, battery compartment 34 comprises an elongated chamber within handle 26 for receiving cells 30-33 in a linear, axially aligned, end-to-end arrangement as illustrated. An elongated, generally rectangular battery compartment cover 36 is provided for enclosing the battery compartment and is removably hinged to housing 16 by means of a pair of projecting tabs, 37 and 38, along the rear surface thereof. The tabs are individually received in complementary dimensioned slots 39 and 40 formed in housing 17 adjacent the upper edge of compartment 34. Preferably, cover 36 is dimensioned to form an essentially continuous surface with the lower surface 28 of the receptacle 19 when closed over the compartment.

The interior surface of compartment 34 is curved and conforms generally to the exterior shape of each of the cells 30-33. To maintain precise alignment of each of these cells, a plurality of semi-circular, circumferentially extending, radially projecting ridges 41-48 are formed at spaced intervals on the lower interior surface of compartment 34. The spacing is such that a pair of ridges supports each of the cells 30-33 as shown.

Referring to FIG. 2, each of the cells, in accordance with conventional practice, is seen to comprise a generally cylindrical housing having a positive polarity terminal at one end and a negative polarity terminal at the other. Referring to cell 30 as an example, the positive polarity terminal 49 comprises a raised, generally cylindrical, metallic member protruding from one face of the cell housing in concentric alignment with the linear axis thereof, while the negative polarity terminal 50 comprises a flat metallic region of relatively larger diameter on the opposite face of the cell (FIG. 1). Cells 31-33 are similarly constructed and include positive polarity terminals 51-53 and negative polarity terminals 54-56, respectively. In further accordance with conventional practice, the four cell battery 29 is formed by electrically interconnecting the opposing terminals of adjacent cells within the battery compartment 34.

Battery compartment 34 further includes a plurality of electrical contact assemblies which, in accordance with the invention, electrically contact the terminals of the cells only if the cells are properly oriented within the compartment. At the left end of the battery compartment (as illustrated in FIG. 2) a positive polarity electrical contact assembly 57 is provided for connecting the positive polarity terminal 49 of cell 30 with the circuitry of PSA 10, while at the opposite end of the compartment, a negative polarity electrical contact assembly 58 contacts the negative polarity terminal 56 of cell 33. Midway along the interior of the battery compartment 34, an intermediate electrical contact assembly 59 electrically connects the positive polarity terminal 52 of cell 32 with the negative polarity terminal 54 of cell 31. In accordance with the invention, each of the electrical contact assemblies 57-59 is constructed to be sensitive to the orientation of the cells within the compartment. Accordingly, electrical communication between the battery 29 and the circuitry of PSA 10 will be established only if each of the individual cells is correctly oriented within battery compartment 34.

The construction of the positive polarity electrical contact assembly 57 is illustrated most clearly in FIGS. 3 and 3a. Referring to those figures, the assembly is seen to include a generally disc shaped carrier member 60 slidably received within a circular recess 61 formed in the left end wall of compartment 34 and laterally displaceable therein. Carrier member 60 is formed of a hard, durable insulating material such as plastic and includes a metallic contact member 62 adjacent its center which is electrically connected to the circuitry of PSA 10 (FIG. 1) by means of a soldered connection 63 to a wire conductor 64. A contact surface 65 on contact 62 is arranged to engage the positive polarity terminal of one of the cells. As illustrated, contact 62 is embedded in a generally cylindrical pillar 66 formed on the interior surface 67 of the carrier member 60 adjacent its center. The exterior surface 68 of the carrier member includes a generally circular aperture 69 adjacent its center which exposes a portion of the contact surface 65 to the interior of the battery compartment 34. Preferably, aperture 69 is dimensioned to closely receive the cylindrical positive terminal 50 of cell 30.

To assure positive contact with the battery terminal 50, the carrier member 60 is inwardly biased by means of a coil spring 70 disposed between an interior sidewall 71 of the housing 17 and the interior surface 66 of the carrier member. Movement of the carrier member 60 toward cell 30 is limited by means of a tab 72 formed on the carrier member which engages an abutment 73 formed in recess 61.

When constructed in this manner, the carrier member 60 forms a raised insulating region on the contact surface 65 which prevents physical contact between the contact surface and any structure substantially larger than the positive polarity terminal of one of the cells. Accordingly, the contact surface is thus prevented from contacting the negative terminal of cell in the event the orientation of the cell in the compartment is reversed end-for-end.

The construction of the negative polarity electrical contact assembly 58 is illustrated in FIGS. 3 and 3b. The contact assembly includes a generally disc-shaped contact 74 slidably received within a circular recess 75 formed in the right end wall of compartment 34 and laterally displaceable therein. The contact 74 is preferably formed of a non-tarnishing conductive metal and presents a flat contact surface 76 to the negative polarity terminal 49 of cell 33. Adjacent its center, contact 74 is provided with an aperture 77 extending through both the contact surface 76 and a tubular structure 78 formed opposite thereto. A generally disc-shaped insulator 79 is received in the aperture adjacent contact surface 76 to form an essentially planar surface therewith.

A cylindrical pillar 80 formed on the side wall of the battery compartment is received in the remainder of the aperture and serves to guide contact 74 as it is laterally displaced in recess 75. The contact is outwardly biased toward battery terminal 49 by means of a helical spring 81 disposed around pillar 80 between the compartment end wall and the contact. Lateral movement of the contact is limited by means of a downwardly depending tab 82 formed thereon and an abutment 83 formed in recess 75.

In accordance with one aspect of the invention, the diameter of insulator 79 is greater than the diameter of the positive polarity terminals on each of the cells 30–33. Insulator 79 thus forms an insulating region on the contact surface 76 which prevents electrical contact to the positive polarity terminal 48 of cell 33 in the event the cell is misoriented in the battery compartment.

The intermediate electrical contact assembly 59 is illustrated in FIGS. 3 and 3c and is seen to comprise a partition 84 extending across battery compartment 34 between the adjacent ends of cells 31 and 32. The partition is formed of a durable insulating material and can be integrally molded in compartment 34 as illustrated. Alternatively, the partition can comprise a separate member removably insertable within slots (not shown) formed in the side walls of the compartment.

The function of the intermediate electrical contact assembly 59 is to electrically connect the positive polarity terminal 52 of cell 32 with the negative polarity terminal 54 of cell 31 only when the cells have the respective orientations illustrated. To this end, a generally disc shaped contact 85 is mounted to the side of partition 73 opposite the negative polarity terminal of cell 31. Contact 85 comprises a generally flat, metallic, electrically conductive member having a cup-shaped depression 86 adjacent its center. The circumferential edge 87 of the contact member is turned down as illustrated to form a rim which is received in a complementary dimensioned circular channel 28 formed in the face of partition 84 adjacent cell 31. The cup-shaped depression 86 receives an insulating member 89, and is shaped to form an essentially contiguous contact surface 90 having a circular insulating region adjacent its center.

The surface of the partition 84 adjacent the positive polarity terminal 52 of cell 32 is provided with an aperture 91 adjacent its center which exposes a portion of contact 84. The aperture is dimensioned to receive the positive polarity terminal 52 and is sufficiently shallow as to permit the terminal to contact the exposed region of contact 85. It will be appreciated that the intermediate contact assembly 59 thus combines the operative structural features of positive and negative polarity contacts 57 and 58 into a single structure for interconnecting cells 31 and 32.

Figure 4:
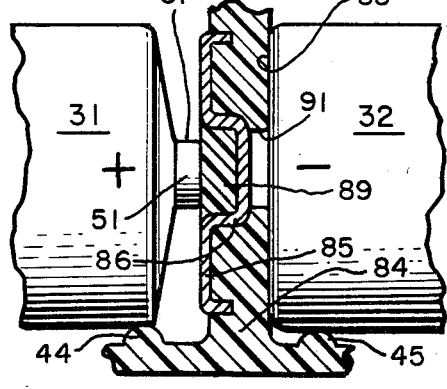
FIG. 4 is a fragmentary view, partially in section, of a battery terminal constructed in accordance with the invention shown in conjunction with a pair of incorrectly oriented electrochemical cells, useful in understanding the operation of the battery compartment.

In view of the foregoing description, it will be apparent that because of the shape and location of each of the contact assemblies 57, 58 and 59, cells 30–33 will be electrically connected with one another, and with the circuitry of PSA 10, only when they are properly oriented within battery compartment 34 as illustrated in FIG. 2. In the event one or more of the cells is incorrectly oriented, the construction of the adjacent contact is such that no electrical connection will be made to the improperly oriented cell. For example, in FIG. 4, cells 31 and 32 have each been improperly oriented within the battery compartment. It will be apparent that because of the circular insulator 89, no electrical connection will be established between the positive polarity terminal 51 and the contact 85. Similarly, no electrical connection will be established between contact 85 and the negative polarity terminal 55 of cell 32 since the projection of partition 84 beyond the exposed portion of contact 85 prevents contact between the battery terminal and the contact.

In the event cell 30 is misoriented, no connection will be established between negative polarity battery terminal 53 and contact 65 since the exterior surface 68 of the carrier member 60 extends beyond the exposed surface of the contact. Similarly, in the event cell 33 is misoriented, the circular insulator 79 will engage the positive polarity terminal 48 of the cell and thus will insulate the cell from contact 76.

Figure 5:
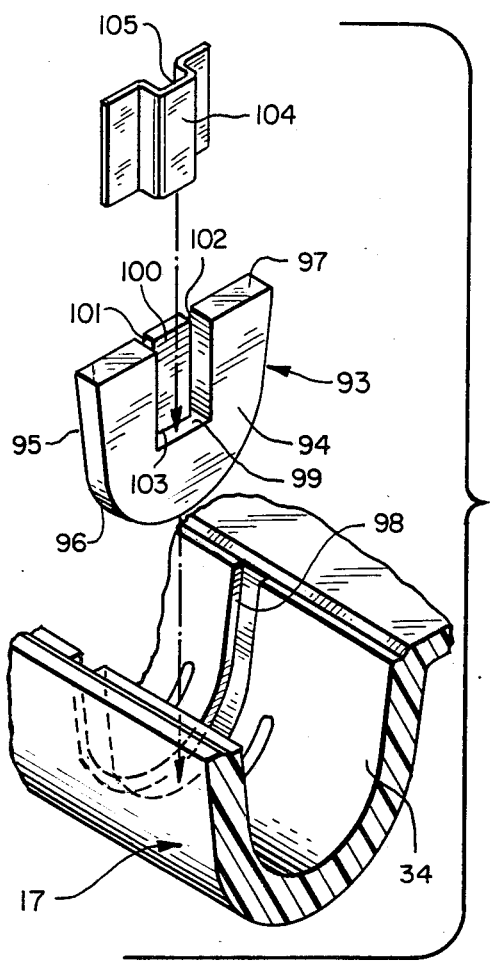
FIG. 5 is an exploded fragmentary perspective view of an alternative construction of the battery compartment constructed in accordance with the invention.
Figure 6:
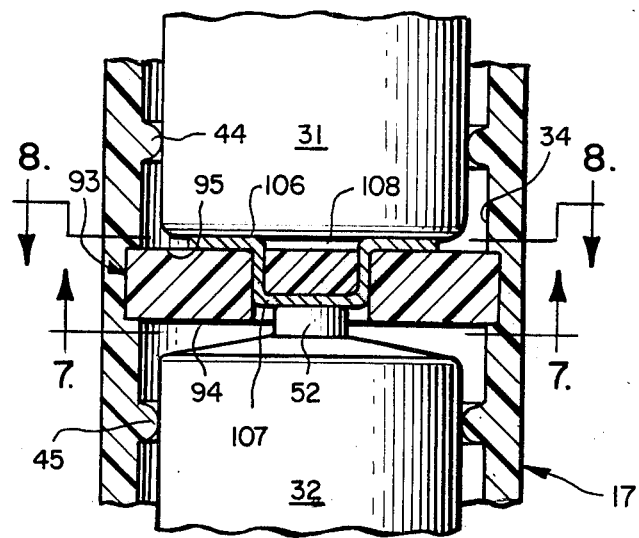
FIG. 6 is a fragmentary sectional view of the alternate construction illustrated in FIG. 5.

Referring to FIGS. 5–8, an alternative construction of the intermediate electrical contact assembly is illustrated. As shown, the alternative intermediate contact assembly includes a removable insert member 93 which forms a partition across the battery compartment between the positive polarity terminal of cell 32 and the negative polarity terminal of cell 31 (FIG. 6). Insert 93 comprises a generally planar member, preferably formed of a rigid, insulating plastic, having a pair of opposed planar faces 94 and 95 and an arcuate lower edge 96 which generally conforms to the cross sectional shape of the battery compartment. The upper edge 97 of the insert is generally flat as illustrated.

The inner surface 34 of the battery compartment 34 of the battery compartment is provided with a generally rectangularly-sectioned groove 98 which is dimensioned to receive insert member 93 and hold the member rigidly in place between adjacent cells 31 and 32. Preferably, the dimensions of groove 98 and of the insert member are such that sufficient friction exists to hold the member in place regardless of the orientation of the PSA unit.

Referring further to FIG. 5, face 94 of the insert member 93 is provided with a generally rectangular recess 99 which extends perpendicularly downwardly from upper edge 97. As illustrated, the recess does not extend fully through the insert member but rather extends only partly therethrough so as to form a generally rectangular, uppwardly extending tab 100. A pair of slots 101 and 102 are formed on each side of tab 100 and extend fully through the insert member such that only the lowermost edge 103 of the tab remains attached to the remainder of the insert member. Accordingly, tab 100 is inwardly deflectable relative to face 95 of the insert member.

To provide electrical contact between the respective terminals of cells 31 and 32, an electrical contact member 104 is provided which is adapted to engage insert member 93. As shown, contact member 104 preferably consists of a single, electrically conductive metallic strip in which a generally rectangularly-sectioned channel 105 has been formed along the vertical midline thereof. Preferably, channel 105 is dimensioned to receive tab 100 while the thickness of contact member 104 closely matches the width of each of the slots 101 and 102. The vertical dimension of the contact member closely matches the vertical dimension of recess 99 and of tab 100.

When so constructed, electrical contact member 104 can be inserted into inset member 93 as illustrated in FIG. 6. When so inserted, one side 106 of member 104 will face the negative polarity terminal of cell 31 while the other side 107 will face the positive polarity terminal 52 of cell 32. As shown in FIG. 6, the depth of channel 105 is such that the distance between sides 106 and 107 of the contact member is less than the total thickness of insert member 93. Accordingly, when thus assembled, side 107 will be slightly recessed beneath face 94 of the insert member while side 106 will extend slightly beyond the outer face 108 of tab 100. Thus, when cells 31 and 32 are oriented as illustrated in FIG. 6, the respective terminals will contact the exposed surfaces 106 and 107 so as to establish electrical continuity between the cells. If however the orientation of either cell is incorrect, contact between either of the cell terminals and the electrical contact member 104 will not occur. It will be appreciated that in order to assure a good mechanical contact between cell 32 and the contact member, the width of channel 105 formed in member 104 is preferably greater than the diameter of positive polarity terminal 52.

Figure 7:
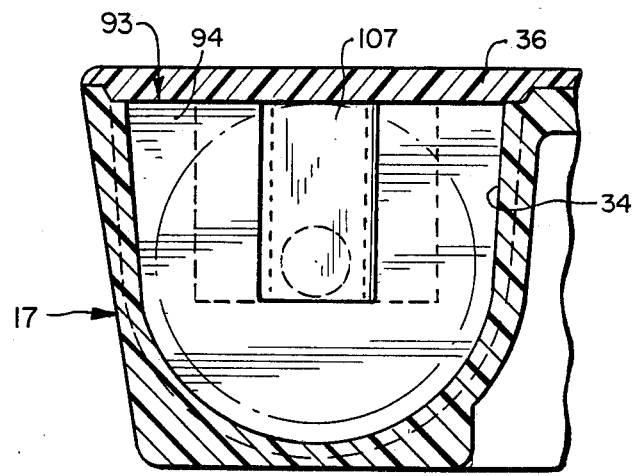
FIG. 7 is a sectional view of the alternate construction illustrated in FIG. 6 taken along line 7—7 thereof.
Figure 8:
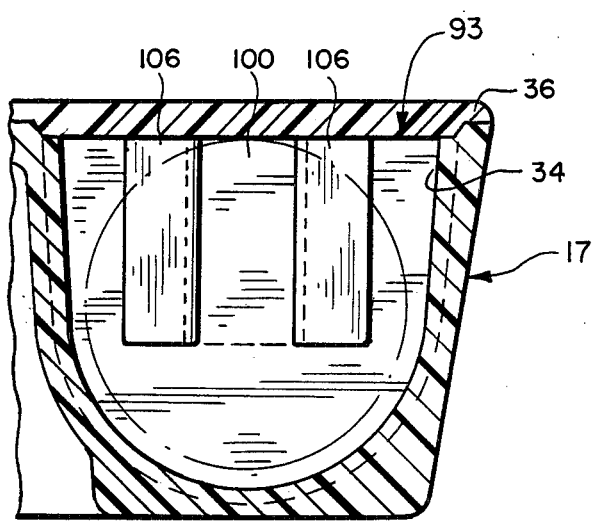
FIG. 8 is a sectional view of the alternate construction illustrated in FIG. 6 taken along line 8—8 thereof.

FIGS. 7 and 8 illustrate the exposed area of electrical contact member 104 on either side of insert member 93.

As shown in FIG. 7, contact member 104 is exposed only adjacent the center of the member and therefore is available for contact by the positive polarity terminal of an electrochemical cell. As shown in FIG. 8, electrical contact member 104 is exposed on opposite sides of tab 100 and therefore is available for contact by the negative polarity terminal of an electrochemical cell. This alternative construction of the intermediate contact assembly permits rapid and simple formation of both the electrical contact member 104 and the removable insert member 93 and therefore reduces the time and expense of manufacturing the intermediate contact assembly.

In view of the foregoing, it will be apparent that the battery compartment constructed in accordance with the invention will permit energization of the device circuitry only in the event each of the cells is properly oriented. While a four cell battery has been shown and described for illustrative purposes it will be appreciated that the invention can be adapted for use with anywhere from one to an unlimited number of cells. When a plurality of cells is used, for complete protection it is desirable that an intermediate contact assembly 57, such as the one shown and described, be included between each pair of cells so that each cell is exposed to at least one such polarity sensitive contact assembly.

While it is preferred that intermediate contact assemblies be used between each pair of batteries in conjunction with polarity sensitive contacts at each end of the battery compartment for protection against mis-orientation of any one battery, it will be appreciated that in some applications it may be sufficient to utilize conventional contacts a each end of the compartment and only one polarity-selective contact assembly between a pair of adjacent cells in order to provide protection in the event of misorientation of all of the cells within the compartment.

It will be further appreciated that the general size and shape of the electrical contacts and cooperating insulating structures can be modified without departing from the scope of the invention. For example, each of the contact assemblies can be formed using a flat electrically conductive member on which the conductive and non-conductive areas are defined through application of an applied electrically insulating material such as an insulating paint.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A battery compartment for receiving therein one or more elongate electrochemical battery cells of the type having dimensionally dissimilar terminals of opposite electrical polarity at opposite ends, comprising:
   a housing defining a battery receiving chamber for receiving one or more of the electrochemical battery cells in series connected end-to-end stacked relation;
   electrical contact means at one end of said chamber for electrically engaging the most adjacent terminal of the most adjacent cell received in said chamber when said most adjacent terminal is a predetermined one of said dissimilar terminals, and for preventing electrical engagement to said adjacent terminal when said adjacent terminal is the other of said dissimilar terminals; and additional electrical contact means at the opposite end of said chamber for electrically engaging the other of said dissimilar terminals;

said electrical contact means at one end of said chamber including a first contact surface arranged to engage the predetermined one of said dissimilar terminals and a first insulating region overlying at least a portion of that portion of said first contact surface not in contact with said predetermined dissimilar terminal;

said additional electrical contact means including a second contact surface arranged to engage the other of said dissimilar terminals and a second insulating region centrally located on said second contact surface.

2. A battery compartment as defined in claim 1 wherein said chamber is dimensioned and shaped to receive generally cylindrical electrochemical battery cells.

3. A battery compartment as defined in claim 2 wherein said predetermined terminal protrudes from the electrochemical battery cell and said other terminal comprises a generally flat terminal opposite said protruding terminal.

4. A battery compartment for receiving at least one elongated electrochemical battery cell of the type having a protruding terminal of one polarity at one end and a generally flat terminal of opposite polarity at the other end, comprising:

a first electrical contact assembly having a first contact surface arranged to engage the protruding terminal of the cell and having a first insulating region overlying at least a portion of that portion of said first contact surface not in contact with the protruding terminal of the cell;

a second electrical contact assembly having a second contact surface arranged to engage the generally flat terminal of the cell and having a second insulating region centrally located on said second contact surface, said second insulating region being of greater dimension than said protruding battery terminal and of lesser dimension than said flat battery terminal, whereby said first insulating region prevents contact between the flat terminal and said first contact, and said second insulating region prevents contact between the protruding terminal and said second contact assembly when the orientation of the cell is such that the protruding terminal is presented to said second contact.

5. A battery compartment as defined in claim 4 wherein the electrochemical cell is generally cylindrical and the protruding and flat terminals are symmetrically disposed around the elongate axis thereof.

6. A battery compartment as defined in claim 5 wherein said first insulating region projects beyond said first contact region in a direction toward the cell.

7. A battery compartment as defined in claim 6 wherein said second contact surface and said second insulating region together form a substantially flat contiguous surface.

8. A battery compartment as defined in claim 7 wherein said first insulating region projects beyond said first contact region in a direction toward the cell over a distance less than the distance the protruding terminal of the cell extends from the cell.

9. A battery compartment as defined in claim 5 wherein said second contact surface and said second insulating region together form a substantially flat contiguous surface.

10. A battery compartment as defined in claim 5 wherein said compartment receives at least three electromechanical cells and further includes an intermediate contact assembly between the opposing ends of an adjacent pair of cells.

11. A battery compartment as defined in claim 10 wherein said intermediate contact assembly comprises a third contact having opposite sides, one of said sides having a raised insulating region covering all but an area adjacent its center and the other of said sides having an insulating region adjacent its center.

12. A battery compartment for receiving a plurality of elongated generally cylindrical electrochemical battery cells of the type having a protruding generally circular terminal of relatively smaller diameter at one end and a generally circular flat terminal of relatively larger diameter at the other end, comprising:

an insulating partition having first and second spaced parallel spaces positioned between a pair of adjacent battery cells, said second face having a depressed region for receiving the protruding terminal of a battery cell;

a first conducting region on said first face arranged to contact the flat terminal of a battery cell except over a portion of the terminal directly opposite the protruding terminal of the cell;

a second conducting region in said depressed region for contacting the protruding terminal of a battery cell, said second contacting region being recessed from the area of said second face surround said depressed region such that contact between said second conducting region and the flat terminal of a battery cell is prevented; and means for electrically connecting said first conducting region with said second conducting region, whereby an electrical connection between the adjacent terminals of said pair of adjacent battery cells is established only when the flat terminal of one of said cells is adjacent said first conducting region and the protruding terminal of the other of said cells is adjacent said second conducting region.

13. A battery compartment as defined in claim 12 wherein said first conducting region and said first face together form a substantially flat contiguous surface.

14. A battery compartment as defined in claim 13 wherein said first conducting region, said second conducting region and said means for electrically connecting said first and second regions comprise a single conducting member.

15. A battery compartment as defined in claim 14 wherein said conducting member comprises a rigid metallic member having a substantially rectangularly section formed therein such that said first conducting region is displaced from said second conducting region.

16. A battery compartment as defined in claim 15 wherein said insulating partition includes slots for receiving said metallic member.

17. A battery compartment as defined in claim 16 wherein said insulating partition is removably insertable in said compartment.

* * * * *